United States Patent [19]

Mason et al.

[11] Patent Number: 4,731,193
[45] Date of Patent: Mar. 15, 1988

[54] AQUEOUS FOAM CONTAINING CHLORINE DIOXIDE COMPOSITION AND PREPARATION THEREOF

[75] Inventors: John Y. Mason, Plymouth; Bruce W. Hicks, Rio Linda; Donald C. English, Carmichael, all of Calif.

[73] Assignee: Rio Linda Chemical Company, Inc., Sacramento, Calif.

[21] Appl. No.: 879,907

[22] Filed: Jun. 30, 1986

Related U.S. Application Data

[63] Continuation of Ser. No. 636,309, Jul. 31, 1984, abandoned.

[51] Int. Cl.$^4$ .............................................. C11D 3/48
[52] U.S. Cl. ........................................ 252/95; 134/42;
252/90; 252/100; 252/106; 252/187.21; 422/29; 422/37
[58] Field of Search ...................... 134/36, 42; 252/95, 252/100, 103, 106, 187.21, 187.22, 307, 90; 422/29, 37; 423/477; 424/149

[56] References Cited

U.S. PATENT DOCUMENTS

| | | | |
|---|---|---|---|
| 2,392,936 | 1/1946 | Mattin et al. | 134/42 |
| 2,678,922 | 5/1954 | Stone | 252/187.22 X |
| 3,278,447 | 10/1966 | McNicholas | 252/187.21 X |
| 4,084,747 | 4/1978 | Alliger | 252/187.23 X |
| 4,104,190 | 8/1978 | Hartshorn | 252/187.21 |
| 4,330,531 | 5/1982 | Alliger | 424/149 |

*Primary Examiner*—Arthur L. Corbin
*Attorney, Agent, or Firm*—Leonard Bloom

[57] ABSTRACT

An aqueous solution, preferably an aqueous disinfectant solution, containing chlorine dioxide and which is capable of forming a foam, and methods for the preparation and use thereof. An aqueous disinfectant solution capable of forming a foam is prepared adding a foaming agent, i.e., a suitable surfactant, to water. Chlorine dioxide may then be added to the solution or it may be generated in situ by reacting an oxidizing agent, a cationic exchange resin in the acidic form, or an acid with a metal chlorite dissolved therein. The resultant foam solution may subsequently be foamed by being mixed with air in a foam generator. The foam solutions of the instant invention are useful as cleaning and/or sanitizing agents.

2 Claims, No Drawings

AQUEOUS FOAM CONTAINING CHLORINE DIOXIDE COMPOSITION AND PREPARATION THEREOF

This application is a continuation, of application Ser. No. 636,309, filed July 31, 1984, now abandoned.

BACKGROUND OF THE INVENTION

It is widely recognized in commercial packing and food processing plants as well as in the paper and pharmaceutical industries, as well as other industries, that cleaning and/or sanitizing of equipment can be greatly enhanced by the use of foam rather than high pressure sprayed water. It is also common for these industries to utilize both portable and/or central clean-in-place systems to achieve and maintain sanitary conditions.

A portable foam cleaner is usually a batch system, one such system being disclosed in U.S. Pat. No. 3,797,744. Utilizing a plurality of tanks, a foam with or without a sanitizer can be generated. The system utilizes compressed air and chemicals under pressure to generate foam through a foam generator.

A central clean-in-place foam system utilizes a continuous process. The foam generating chemical and the sanitizing chemical are usually educted into a large mixing tank along with the water driving the eductor. An automatic level control activates the eductor water source to keep the tank filled at all times. Feed-rates, and thus concentrations and foam characteristics, can be controlled by use of rotometers. From the mixing tank, the solution is pumped under pressure throughout the plant to the individual foam generating stations. A gas, such as compressed air, is introduced at this point to generate the foam. The foam is then delivered through a hose or otherwise conducted to the surfaces to be cleaned and sanitized. U.S. Pat. No. 3,823,727 discloses one type of foam generating station utilized in a central foam system. Many other types are currently on the market.

The foam covers and adheres to the surface to be cleaned. Some cleahing, penetrating and loosening action can occur, depending on the formulation of the foam generating chemical. To achieve microbiological control, a sanitizer, or disinfectant chemical, is used in the foam system.

One of the advantages of using foam to achieve microbiological control is that, since it adheres to the surface and remains for a period of time, it allows more time for the disinfectant to do its work. Although the foam prolongs the contact time, those disinfectants that have rapid rate of kill are preferred in order to obtain the maximum benefit.

The sanitizing, or disinfectant, chemical is essential in order to obtain the desired destruction of the microorganisms, e.g., bacteria, molds, fungi, spores, and viruses. Common inorganic disinfectants currently in use are exemplified by chlorine and iodine. Examples of organic disinfectants are carbamates or quaternary ammonium compounds. Although the foregoing disinfectants are somewhat effective and are widely used in the current state of the art, they have many limitations. The use of a more powerful, more rapid disinfectant would greatly enhance the sanitizing effectiveness of foam systems.

The use of chlorine dioxide in many disinfection applications is growing widely because of its superior bactericidal, sporicidal, fungicidal, and viricidal properties as well as its extremely fast rate of disinfection. The use of chlorine dioxide in a foam system would greatly enhance the art of sanitizing.

Prior to this invention, the use of chlorine dioxide in foams or foam cleaners for the disinfection of microorganisms was not known. Chlorine dioxide is irritating and has a very noxious odor at concentrations as low as 0.5 ppm in a water system. Moreover, chlorine dioxide does not undergo hydrolysis so its irritating and noxious properties persist. It was previously thought that it was impossible to use chlorine dioxide in an aqueous foam system at relatively high chlorine dioxide concentrations since its strong, unpleasant odor when dissolved in water makes it impossible to spray at concentrations necessary to achieve sanitization in, for example, food processing plants where personnel are working in the close vicinity.

Another reason that chlorine dioxide has not previously been used in a foam system at relatively high chlorine dioxide concentrations is that it is such a strong oxidizing agent that it was thought that it would destroy or break down the organic compounds that make up the foam generating chemical. Another reason that chlorine dioxide has not previously been used in a foam system is that it was thought that the chlorine dioxide would undergo rapid degradation and lose its disinfectant and biocidal properties.

Surprisingly, the use of chlorine dioxide in a foam system, in accordance with the practice of this invention, does not result in any chlorine dioxide odor at relatively high concentrations up to 1200 ppm. Moreover, it does not destroy the organic foam generating compounds. In effect, if formulated correctly, the chlorine dioxide foam solution of this invention is very stable and produces a foam of exceptionally high quality. In addition, it has been found that chlorine dioxide in foam solutions is very stable and remains potent as a biocide for up to at least 72 hours or even longer.

The term "foam solution" as used herein means an aqueous disinfectant solution containing a foam generating chemical and which is capable of producing a foam when mixed with a gas such as air in, for example, a foam generator. The foam generating chemical is typically one or more surfactants. A suitable surfactant may be cationic, nonionic, or anionic, as long as it is capable of forming an aqueous foam. The choice of surfactant is within the skill of the art. The disinfectant is primarily chlorine dioxide.

Three well known reactions for generating chlorine dioxide from sodium chlorite are as follows:

$$2NaClO_2 + Cl_2 \rightarrow 2ClO_2 + 2NaCl \tag{1}$$

$$2NaClO_2 + HOCl \rightarrow 2ClO_2 + NaCl + NaOH \tag{2}$$

$$5NaClO_2 + 4HCl \rightarrow 4ClO_2 + 5NaCl + 2H_2O \tag{3}$$

Equation (1) exemplifies the generation of chlorine dioxide by the action of an oxidizing agent, i.e., chlorine, on a metal chlorite, i.e., sodium chlorite. Equation (2) exemplifies the generation of chlorine dioxide by the action of an oxidizing acid, i.e., hypochlorous acid, on a metal chlorite. Equation (3) illustrates the production of chlorine dioxide by the action of an acid, i.e., hydrochloric acid, on a metal chlorite. It will be understood that the above reactions are not limited to the metal chlorite, oxidizing agents and acids illustrated and that the choice of reactants is within the skill of the art.

By means of the foregoing reactions, chlorine dioxide may be obtained by, for example, use of a commercially available chlorine dioxide generator and dissolved in the foam solution. A chlorine dioxide generating apparatus is described in U.S. Pat. No. 4,247,531. Alternatively, chlorine dioxide may be generated in the foam solution via one of the above reactions.

U.S. Pat. No. 2,392,936 discloses aqueous oxidizing foam solutions which are taught to be useful in decontaminating areas contaminated with, for example, noxious or poisonous chemicals. The disclosed aqueous foam solutions contain a foam generating soap and an oxidizing agent such as sodium chlorite. It is disclosed that the foregoing solution may be acidified by the addition of hydrochloric acid to a pH of about 4. It has been found that when the pH of such a solution has been lowered to about 4, only about 0.5 percent of the sodium chlorite is converted to chlorine dioxide.

SUMMARY OF THE INVENTION

The instant invention provides an aqueous foam solution, preferably an aqueous disinfectant solution, containing chlorine dioxide as the disinfectant. Such foam solutions are capable, when mixed with a gas such as compressed air, of forming stable foams. Moreover, the foam solutions of this invention are stable, retaining disinfectant and biocidal properties for 72 hours and longer. In addition, the foam solutions and foams derived therefrom do not exhibit the noxious odor of chlorine dioxide, even at relatively high chlorine dioxide concentrations.

It is therefore an object of this invention to provide a foam cleaning and disinfectant solution that utilizes chlorine dioxide as a disinfectant.

It is another object of this invention to provide a chlorine dioxide foam solution that utilizes chlorine dioxide in relatively high concentrations with little or no noxious odor.

It is still another object of this invention to provide a chlorine dioxide foam solution where the chlorine dioxide remains stable and retains its disinfectant and biocidal properties over a long period of time.

It is yet another object of this invention to provide foam solutions containing concentrations of chlorine dioxide above about 1500 ppm in situations where personnel are not exposed.

Another object of this invention is to provide a chlorine dioxide foam solution that allows flexibility in the type of foam cleaning accomplished by choice of a high pH foam or low pH foam.

Still another object of this invention is to provide a chlorine dioxide foam solution wherein the chlorine dioxide is generated in the solution by the action of an oxidizing agent on a metal chlorite dissolved in said solution.

Yet another object of this invention is to provide a chlorine dioxide foam solution wherein the chlorine dioxide is generated in the solution by the action of a cationic exchange resin in the acidic form on a metal chlorite dissolved in said solution.

It is still another object of this invention to provide a chlorine dioxide foam solution wherein the chlorine dioxide is generated in the solution by the action of an acid present in an amount sufficient to lower the pH of said solution below about 3.7 on a metal chlorite dissolved in said solution.

Yet other objects will be apparent to those skilled in the art.

The foregoing and other objects are accomplished by the practice of this invention. Broadly, viewed in one of its principal aspects, this invention consists of an aqueous solution having disinfectant properties and the capability of forming a stable foam, said solution comprising a major proportion of water having dissolved therein an effective amount of a foam generating agent and an effective amount of chlorine dioxide wherein said chlorine dioxide may be generated outside the solution and subsequently dissolved therein, or it may be generated within the solution by the action of an oxidizing agent or a cationic exchange resin in the acidic form on a metal chlorite dissolved in said solution, or it may be generated within the solution by the action of an acid present in an amount sufficient to lower the pH of said solution below about 3.7 on a metal chlorite dissolved in said solution.

The aqueous foam solution of this invention may be used to clean and disinfect a surface in need thereof in accordance with the following steps:

1. An aqueous disinfectant solution comprising a major proportion of water, an effective amount of a foam generating agent, and an effective amount of chlorine dioxide is mixed with a gas in a foam generator to thereby form a disinfectant foam;
2. Said disinfectant foam is sprayed on the surface to be treated;
3. The disinfectant foam is allowed to remain in contact with said surface for a period of time sufficient to allow cleaning and disinfection thereof, and
4. Said disinfectant foam is thereafter removed from said surface.

The instant invention thus provides an aqueous solution having disinfectant and biocidal properties and the capability of forming a foam as well as a method of cleaning and disinfecting a surface in need thereof by contacting said surface with said disinfectant foam. The invention is characterized by the use of chlorine dioxide as the disinfectant. The disinfectant foam solutions of the invention are stable, with the chlorine dioxide retaining its disinfectant and biocidal properties over long periods of time. Moreover, the foam solutions and foams derived therefrom do not have the noxious odor of chlorine dioxide, even at relatively high chlorine dioxide concentrations. In addition, the disinfectant foam solutions of the invention are capable of forming stable foams.

The nature and substance of the present invention as well as its objects and advantages will be more clearly perceived and fully understood by referring to the following description of the preferred embodiments.

DESCRIPTION OF THE PREFERRED EMBODIMENTS

The instant invention provides for continuous or batch processes for the production of aqueous disinfectant foam solutions containing an organic foam generating agent, typically a surfactant, and chlorine dioxide. The solutions may also contain various organic or inorganic penetrants, solvents, additional detergents, couplers, and cleaning compounds to enhance the disinfection and cleaning capability of the foam.

The foam solution of the invention may be prepared by generating the chlorine dioxide outside the solution and subsequently dissolving it therein. The chlorine dioxide may be obtained by use of a commercially available chlorine dioxide generator such as that disclosed in U.S. Pat. No. 4,247,531. The chlorine dioxide may alternatively be obtained by use of a stabilized chlorine dioxide solution or by use of chlorine dioxide-releasing chemicals. Foam solutions where the chlorine dioxide is prepared outside the solution and subsequently added may be either acidic or basic.

The foam solution of the invention may be an acid-coupled foam solution containing approximately 2% to about 20% by weight of inorganic acid, preferably about 4% to about 14% by weight of inorganic acid; about 1% to about 15% by weight of foam generating agent; and about 1% to about 20% by weight of cleaning and disinfection enhancement compounds such as penetrants, solvents, and alkaline cleaners. In an acid-coupled foam solution, the foam generating agent is an anionic surfactant such as an organic acid in the free acid form and coupled with an inorganic, or mineral, acid. The acid-coupled foam solution is mixed with a solution containing about 1% to about 25% by weight of a water soluble metal clorite, preferably about 10% to about 15% by weight of metal chlorite, in such a ratio of acid-coupled foam solution to metal chlorite solution as to provide a final solution having a pH below about 3.7 to thereby obtain about 10 to about 1500 mg./l of chlorine dioxide and preferably about 15 to about 500 mg./l of chlorine dioxide in the foam solution. It is critical to the practice of this invention that when chlorine dioxide is generated in the aqueous foam solution by the action of an acid on a metal chlorite dissolved in said solution, the pH of the final solution be below about 3.7. If the pH is above about 3.7, only an insignificant amount of metal chlorite is converted to chlorine dioxide. It is preferred that the pH of the final solution be within the range of about 1 to about 3.5, with a pH of about 2.5 being most preferred.

The foam solution of this invention may alternatively be alkaline. Such alkaline foam solutions contain about 2% to about 20% by weight of foam generating agent, about 1% to about 20% by weight of a caustic material such as sodium hydroxide, and about 1% to about 20% by weight of disinfection and cleaning enhancement compounds. The alkaline foam solutions preferably contain about 5% to about 15% by weight of foam generating agent, about 5% to about 12% by weight of caustic material, and about 4% to about 14% by weight of disinfection and cleaning enhancement compounds. This solution is added in an amount of about 0.01 to about 5.0 oz. per gallon, preferably about 0.05 to about 2.0 oz. per gallon, to water containing about 10 to about 1500 mg./l, and preferably about 15 to about 500 mg./l, of chlorine dioxide.

It is within the scope of this invention to generate the chlorine dioxide in the foam solution. An aqueous solution containing a foam generating agent and a water soluble metal chlorite may be reacted with an aqueous solution containing an acid in an amount such that the final solution has a pH below about 3.7; it may be passed through a column containing a cationic exchange resin in the acidic form, or it may be reacted with an oxidizing agent such as chlorine or a solution containing an oxidizing acid, e.g., a solution containing an acid, and a water soluble metal hypochlorite, i.e., a hypochlorous acid solution. The water soluble metal chlorite is preferably an alkali metal chlorite such as lithium chlorite, sodium chlorite, or potassium chlorite; or an alkaline earth metal chlorite such as calcium chlorite, magnesium chlorite, or barium chlorite. The acid may be a mineral acid such as hydrochloric acid, sulfuric acid, or boric acid; it may be an organic acid such as oxalic acid, acetic acid, or citric acid; or it may be an acidic salt such as sodium bicarbonate, potassium dihydrogen phosphate or sodium bisulfate as well as any combination of the foregoing acids provided the final solution has a pH below about 3.7. Examples of cationic exchange resins are commercial cationic exchange resins in the acid form. The water soluble metal hypochlorite is preferably an alkali metal hypochlorite such as lithium hypochlorite, sodium hypochlorite, or potassium hypochlorite; or an alkaline earth metal hypochlorite such as calcium hypochlorite, magnesium hypochlorite, or barium hypochlorite. The metal hypochlorite is reacted with a mineral acid such as hydrochloric acid or an organic acid such as acetic acid to form hypochlorous acid.

When a foam solution of this invention is prepared as described above, the resulting solution may contain chlorous acid and chlorite ion in addition to chlorine dioxide. Chlorous acid and chlorite ion are beneficial as biocides and foam solutions containing them are within the scope of this invention.

The aqueous solution containing foam generating agent and metal chlorite contains about 1% to about 20% by weight and preferably about 10% to about 15% by weight of foam generating agent, about 1% to about 15% by weight, and preferably about 3% to about 9% by weight, of metal chlorite; with the remainder of the solution being made up of cleaning and disinfection enhancement compounds dissolved in water.

The acid solution that is reacted with the above solution of foam generating agent and metal chlorite preferably has a concentration of about 1% to about 50% by weight of acid and, more specifically, a concentration of about 20% to about 40% by weight of acid.

The metal hypochlorite solution that is prereacted with an acid before contact with the metal chlorite-bearing foam solution contains between about 1% and about 40% by weight, and preferably between about 7% and about 16% by weight, of metal hypochlorite.

In any event, the foregoing solutions are reacted in such ratios and subsequently diluted to yield a foam solution containing about 10 to about 1500 mg./l of chlorine dioxide and preferably about 15 to about 500 mg./l of chlorine dioxide and which is stable over at least a 72 hour period while retaining its foaming ability and chlorine dioxide content.

The aqueous solution containing foam generating agent and metal chlorite may also be reacted with an oxidizing agent such as bromine or preferably chlorine to thus generate chlorine dioxide in the foam solution. The solution of foam generating agent and water soluble metal chlorite broadly contains about 1% to about 20% by weight of foam generating agent, about 1% to about 15% by weight of metal chlorite, and about 1% to about 20% by weight of cleaning and disinfection enhancement compounds. Preferably, the solution contains about 5% to about 15% by weight of foam generating agent, about 3% to about 8% by weight of metal chlorite, and about 5% to about 15% by weight of disinfection and cleaning enhancement compounds. The solution of foam generating agent and metal chlorite is brought together with chlorine in a prereaction column and is subsequently diluted with water to the desired concentration. The reactants are brought together in such a ratio as to provide a stable foam solution containing about 1 to about 1500 mg./l of chlorine dioxide, and preferably about 15 to about 500 mg./l of chlorine dioxide. It has been noted in water treatment that sometimes the use of chlorine dioxide in combination with chlorine is superior to the use of either separately, so for some applications it is advantageous to add excess chlorine to the reaction mixture. Thus, it is advantageous in certain applications to have the foam solution contain up to about 500 mg./l of chlorine, and preferably up to about 250 mg./l of chlorine. As described above, in this embodiment where an oxidizing agent such as chlorine is used, the water soluble metal chlorite is preferably an alkali metal chlorite or an alkaline metal earth chlorite.

Examples of disinfection enhancement agents used in the foam solutions of this invention are penetrants such as the free acid forms of phosphate esters and sodium hexalene sulfonate that enhance the ability of the chlorine dioxide to penetrate slime layers and give a more complete kill.

Examples of cleaning enhancement compounds that are used in the foam solutions of this invention are hexalene glycol, sodium xylene sulfate, sodium tripoly phosphate, sodium metasilicate, sodium silicate, tetrasodium ethylenediamine tetraacetate, sodium glucoheptanate, tetrapotassium polyphosphate, alkyl sulfonates and fatty alcohol sulfates.

Examples of solvents are hexalene glycol, castor oil, ethylene glycol polymers and short and medium length alcohols.

Examples of couplers used in the foam solutions of this invention are free acid and salt forms of phosphate esters, sodium triethanolamine, alkoxylated lanolin and sodium xylene sulfonate.

As mentioned above, the foam generating agent of this invention is a surfactant which may be a cationic surfactant, a nonionic surfactant, or an anionic surfactant. Examples of nonionic surfactants are polyvinyl alcohol, polyvinyl pyrrolidone and nonylphenoxy polyethanol. Examples of suitable anionic surfactants are linear alkyl sulfonates and alkyl-substituted aromatic sulfonate such as dodecylbenzene sulfonate. Examples of suitable cationic surfactants are alkyl quaternary ammonium salts and the coconut oil acid ester of sodium isothionate.

The nature and substance of the instant invention as well as its objects and advantages will be more clearly understood by referring to the following specific examples.

EXAMPLE I

A foam solution was prepared by adding 0.75 fluid ounces of a foam generating agent comprising a linear alkyl sulfonate, sodium xylene sulfonate which is an ionic-nonionic coupler, sodium hexalene sulfonate which is a penetrant, and sodium hydroxide to 1 gallon of water containing 150 mg./l of chlorine dioxide. Chlorine dioxide concentration was measured by ampermetric titration as described in "Chemistry in Water Reuse," Chapter 21, by Roberts and Aieta. The chlorine dioxide foam solution was then passed through a booster pump at a rate of flow of 3 gallons per minute (gpm) under a pressure of 60 psig. After passing through a check valve in the line, air was added at 60 psig to the foam solution to form a foam spray. A 7,200 cubic foot room was sprayed with the foam which was left in place for 5 minutes. A total of 8,516 mg. of chlorine dioxide should have been released into the room, resulting in 0.12 ppm of chlorine dioxide in the air, an amount that should have been easily detected by odor. There was no detectable odor of chlorine dioxide in the room.

The above experiment was repeated with foam solutions containing various concentrations of chlorine dioxide up to 1200 mg./l of chlorine dioxide. The results were the same as those obtained using the foam solution containing 150 mg./l of chlorine dioxide. It should be noted that 1200 mg./l of chlorine dioxide was chosen as the practical upper limit in the foregoing experiments due to economic considerations, not because of an odor problem.

EXAMPLE II

A chlorine dioxide foam solution was prepared by passing 10 parts by volume of an acidic foam concentrate containing 78.99 percent by weight of water, 13.7 percent by weight of dodecylbenzene sulfonic acid, and 7.31 percent by weight of nonylphenoxypolyethanol through a prereaction column with 1 part by volume of a 15% by weight solution of sodium chlorite. The resultant solution had a pH below 3.7. After passing through the prereaction column, the foam concentrate was diluted with water in a ratio of 1 part by volume of concentrate to 125 parts by volume of water resulting in a foam solution containing 70 mg./l of chlorine dioxide and 10 mg./l of chlorous acid. The foam solution was then passed through the foam generator described in Example I and the resultant foam sprayed onto a can palletizer and feed belt. Both the palletizer and the feed belt had a heavy mold covering that had been previously treated with a solution containing 5000 mg./l of sodium hypochlorite without success. The chlorine dioxide foam was left in contact with the palletizer and feed belt for 5 minutes, resulting in a complete kill of the mold. Mold kill was judged by the ease of removal of the mold from the affected surfaces, and by before and after regrowth of molds judged by plates taken.

EXAMPLE III

A chlorine dioxide foam solution was prepared by passing 10 parts by volume of an acidic foam concentrate containing 56.35% by weight of water, 14.03% by weight of dodecylbenzene sulfonic acid, 7.8% by weight of nonylphenoxypolyethanol, 1.72% by weight of hexamethylene glycol, 2.45% by weight of sulfuric acid and 1.65% by weight of sodium xylene sulfonate through a reaction column with 7.5 parts by volume of a solution containing water, 14.8% of sodium chlorite, and 2.2% sodium hexalene sulfonate. The resultant solution had a pH below 3.7. The foam concentrate was subsequently diluted with water at a ratio of 128 parts by volume of water to 1 part by volume of foam concentrate, resulting in a chlorine dioxide concentration of 145 mg./l and a chlorous acid concentration of 325 mg./l The foam solution was passed through a foam generator as described in Example I and the resultant foam was sprayed onto a cement wall with a heavy slime buildup. The foam was allowed to remain in contact with the wall for a ten minute period. The wall was then sprayed with water to remove the foam. Complete slime kill down to the bare cement was achieved.

EXAMPLE IV

The foam solution of Example III was again prepared, this time having a chlorine dioxide concentration of 147 mg./l and a chlorous acid concentration of 310 mg./l The foam solution was passed through a foam generator as described in Example I and the resultant chlorine dioxide foam was used in an area consisting of a sump with cement walls and metal fixtures. Both walls and fixtures were covered with ⅛–⅜ inches of mold (geotrichum, aspergillus niger). Plates were taken on five sites in the area before the beginning of the test to quantify the viability of the mold. Sites one and two were treated with a foam solution containing 483 mg./l of chlorine. Sites three and four were treated with the foregoing chlorine dioxide foam solution containing 147 mg./l chlorine dioxide and 310 mg./l chlorous acid. Site five was selected as a control with treatment of a non-biocide bearing foam. The foam solutions were allowed to stand for five minutes, and were then rinsed with potable water to remove the foam. Plates were then taken at all sites. After incubation the plates were evaluated for mold growth. All sites except for site 5 showed a reduction in mold growth. The sites treated with chlorine dioxide bearing foam showed significantly less growth than the sites treated with the chlorine bearing foam. Immediately after completion of the first test, site 1 was again treated with a foam bearing 483 mg./l of chlorine, sites 2, 3, and 4 with a foam bearing 147 mg./l of chlorine dioxide and 54 mg./l of chlorite ion. Site 5 was again chosen as a control, and treated with a non-biocidal foam. Again plates were taken and incubated and evaluated. The sites treated with chlorine dioxide in both tests (sites 3 and 4) showed the least growth followed by site 2, site 1, and site 5 in increasing order of growth.

EXAMPLE V

In accordance with the teaching of U.S. Pat. No. 2,392,936, 62.5 g. of 10 weight percent of technical sodium chlorite solution, 31.75 g. of foaming agent (10 weight percent of dodecylbenzene sulfonic acid in water with enough sodium hydroxide added to give a pH of 6.5–7.0), and 0.75 ml. of 35% hydrochloric acid were dissolved in water. The resultant solution had a Ph in the range of 3.7–4.0. The solution was allowed to react for 15 minutes and then analyzed in accordance with the procedure of Aieta, Roberts and Hernandez, *AWWA JOURNAL,* Volume 76, No. 1 (January, 1984). It was found that 0.5% of the chlorite ion was converted to chlorine dioxide, 24.7% was converted to chlorate ion, no chlorine was formed, and 72.3% of the chlorite ion remained unchanged. The balance was presumed to have been converted to chloride ion.

In contrast to the above and in accordance with the practice of this invention, 5 parts of an aqueous solution containing 14.03% of dodecylbenzene sulfonic acid, 7.8% of a phosphate ester, 9.72% of hexamethylene glycol, 2.45% of hydrochloric acid, and 3.86% of sodium xylene sulfonate was reacted with 1 part of a solution containing 18.5% of technical sodium chlorite, 2.2% of sodium xylene sulfonate, and 79.3% of water. The resultant solution had a pH of 2.3. The solution was allowed to react for 15 minutes and analyzed as above. It was found that 48.5% of the chlorite ion was converted to chlorine dioxide, 11% was converted to chlorate ion, and 28.3% remained unreacted. The balance was again presumed to have been converted to chloride ion. It is seen that, by the practice of this invention, the conversion of metal chlorite to chlorine dioxide by the action of an acid is approximately 100 times greater than that achieved by the method disclosed in U.S. Pat. No. 2,392,936.

EXAMPLE VI

Five parts of a solution containing 75.5% water, linear alkyl sulfate 9.59%, hexalene glycol 6.93%, 0.32 tetrasodium ethylamine-diamine tetra acetate, 5.04% of a phosphate ester, 2.5% sodium hydroxide was educted into a reaction column with one part of a solution containing 14.8% sodium chlorite, 2.2% sodium xylene sulfonate, and 83% water. Enough chlorine gas to react stoichiometrically with the chlorite present by the following equation was also educted into the reaction column.

$$2NaClO_2 \text{ and } Cl_2 \rightarrow 2ClO_2 + 2NaCl$$

The resultant solution was diluted in the venturi at a ratio of 106:1 with water. Eighty-nine percent of the chlorite ion feed was converted to chlorine dioxide, 4.5% to chlorate ion, and 6.5% remained unreacted. This corresponds to 174 mg/l $ClO_2$, 11.0 mg/l $ClO_3-$, and 12.7 mg/l $ClO_2-$ in the final foam solution. The final pH of the foam solution was 11.4.

It should be noted that the chlorine-chlorite reaction is independent of pH and that excess chlorine could be easily added to the foam solution through the reaction column in this embodiment of the invention.

EXAMPLE VII

One part of a solution containing 49 grams/L NaOCl was educted with one part of a solution containing 95 grams/l $NaClO_2$ through a column with a hydrogen ion bearing cation exchange resin. The contact time allowed in the column was less than 30 seconds. The resultant solution was diluted 1 part to 22 parts of water and with 1 part of a solution containing water 75.55%, linear alkyl sulfonate 9.59%, hexalene glycol 6.93%, 0.32% tetrasodium ethylamine-diamine tetra acetate, 5.04% of a phosphate ester and 2.5% sodium hydroxide. The resulting foam solution contained 199 mg/l $ClO_2$, 65 mg/l $Cl_2$, and 74 mg/l Chlorite ion. This corresponds to a 71% conversion of chlorite to chlorine dioxide.

Thus, this invention provides an aqueous solution having disinfectant and biocidal properties and the capability of forming a foam as well as a method of cleaning and disinfecting a surface in need thereof by contacting the surface with said disinfectant foam. The invention is characterized by the use of chlorine dioxide as the disinfectant. The chlorine dioxide may be prepared in a commercially available chlorine dioxide generator and dissolved in the foam solution. Alternatively, the chlorine dioxide may be formed in the foam solution by the reaction of chlorine dioxide-releasing chemicals. The disinfectant foam solutions of the invention are stable, with the chlorine dioxide retaining its disinfectant and biocidal properties over long periods of time. Moreover, the foam solutions and foams derived therefrom do not have the noxious odor of chlorine dioxide, even at relatively high chlorine dioxide concentrations. In addition, the foams formed from the disinfectant foam solutions of this invention are surprisingly stable.

While specific embodiments of the present invention have been shown and described in detail to illustrate the utilization of the inventive principles, it is to be understood that such showing and description have been offered only by way of example and not by way of limitation. Protection by Letters Patent of this invention in all its aspects as the same are set forth in the appended claims is sought to the broadest extent that the prior art allows.

We claim as our invention:

1. A foam composition containing chlorine dioxide for cleaning and disinfecting purposes, said composition being comprised of:

five parts of a first aqueous solution containing approximately 14.03% dodecylbenzene sulfonic acid, 7.8% of a phosphate ester, 9.72% of hexamethylene glycol, 2.45% of hydrochloric acid, 3.86% of sodium xylene sulfonate and 62.14% of water;

one part of a second aqueous solution containing approximately 18.5% of technical sodium chlorite, 2.2% of sodium xylene sulfonate and 79.3% water; and six hundred and twelve parts of water.

2. A method of preparing a foam composition containing chlorine dioxide for cleaning and disinfecting purposes, comprising the steps of:

first, preparing a first aqueous solution containing approximately 14.03% dodecylbenzene sulfonic acid, 7.8% of a phosphate ester, 9.72% of hexamethylene glycol, 2.45% of hydrochloric acid, 3.86% of sodium xylene sulfonate and 62.14% of water;

second, preparing a second aqueous solution containing approximately 18.5% technical sodium chlorite, 2.2% sodium xylene sulfonate and 79.3% water;

third, mixing five parts of the first aqueous solution with one part of the second aqueous solution;

fourth, reacting the mixture of the first aqueous solution and the second aqueous solution for fifteen minutes;

fifth, diluting the reacted first and second mixtures with six hundred and twelve parts of water; and sixth, mixing the diluted, reacted mixture of the first aqueous solution and the second aqueous solution, thereby forming the cleaning and disinfecting foam composition containing chlorine dioxide.

* * * * *